(12) United States Patent
Peyman et al.

(10) Patent No.: US 7,316,676 B2
(45) Date of Patent: Jan. 8, 2008

(54) TREATMENT OF RETINAL DETACHMENT

(75) Inventors: Gholam A. Peyman, 8654 Pontchartrain Blvd., Apartment 1, New Orleans, LA (US) 70124; Charalampos Livir-Rallatos, Athens (GR)

(73) Assignee: Gholam A. Peyman, Tucson, AZ (US)

( * ) Notice: Subject to any disclaimer, the term of this patent is extended or adjusted under 35 U.S.C. 154(b) by 718 days.

(21) Appl. No.: 10/224,016

(22) Filed: Aug. 20, 2002

(65) Prior Publication Data

US 2004/0039253 A1 Feb. 26, 2004

(51) Int. Cl.
*A61M 31/00* (2006.01)

(52) U.S. Cl. .................. 604/521; 604/506; 604/117; 604/174

(58) Field of Classification Search .............. 604/521, 604/19, 21–22, 27–28, 35–36, 38–44, 500, 604/513, 117, 164.01, 164.04, 174, 264, 272, 604/278, 286, 540, 541; 606/108
See application file for complete search history.

(56) References Cited

U.S. PATENT DOCUMENTS 3,528,410 A * 9/1970 Banko ........................ 601/2
5,817,075 A * 10/1998 Giungo ..................... 604/294
2002/0133184 A1* 9/2002 LoRusso ................... 606/167
2002/0198511 A1* 12/2002 Varner et al. ............. 604/521

OTHER PUBLICATIONS

Peyman et al., *Vitreoretinal Surgical Techniques*, 2001, Chapters 1-8, pp. 3-96.

* cited by examiner

Primary Examiner—Catherine S. Williams
(74) Attorney, Agent, or Firm—Thompson Hine LLP

(57) ABSTRACT

An apparatus and minimally invasive method for removing fluid from a subretinal space to allow a detached retina to flatten. An apparatus, comprising a fluid withdrawal device and a guide for advancing and placing the device, is positioned on the exterior eye surface at the detachment site. Various embodiments of the apparatus are disclosed. Using the guide, the surgeon advances the device into the fluid-filled space and drains fluid, allowing the retina to flatten. Additional injection of saline or gas into the vitreous cavity normalizes intraocular pressure, and the patient is ambulatory immediately afterward. Unlike other retinal attachment techniques, in the inventive procedure the patient receives only a local anesthetic, and has no restraint on head movement.

17 Claims, 3 Drawing Sheets

TREATMENT OF RETINAL DETACHMENT

FIELD OF THE INVENTION

The invention relates to a method and apparatus for treatment of retinal detachment that permits a patient to be ambulatory immediately after treatment.

BACKGROUND

Retinal detachment occurs when the sensory layers of the retina become separated from their underlying supporting tissue of retinal pigment epithelium and the choroid. Generally, retinal detachment is caused by a retinal tear or the presence of vitreous traction, either of which may occur spontaneously or may be due to trauma. Retinal detachment may also result from pathology, such as retinopathy of prematurity in premature infants or diabetic retinopathy in diabetic individuals. Symptoms of retinal detachment are painless and sudden segmental or total visual loss in one eye.

When there is a tear, or when there is traction causing separation of the retina from its underlying structures, the liquid vitreous passes through the opening and into the subretinal space, inducing further exudation in the subretinal space. The retina gradually separates and detaches from the underlying retinal pigment epithelium. This deprives the outer retina of its normal supply of oxygen and nutrients from the choroid. With time, retinal detachment also results in loss of vision, due to loss of photoreceptor cells located in the outer part of the retina.

Treatment of retinal detachment involves reestablishing the connection between the sensory retina and its underlying supporting tissue. If a detached retina is not timely repaired, the retinal pigment epithelium and glial cells proliferate, forming fibrous bands under and in front of the retina which hold the retina in a fixed and detached position. Therefore, in primary or chronic retinal detachment, a goal of treatment is to reattach the retina as quickly as possible after detachment occurs.

Treatment methods to reattach a detached retina include scleral buckling, pneumatic retinopexy, and vitrectomy with the use of a tamponading agent. None of these methods is entirely satisfactory.

Retinal reattachment by scleral buckling involves an invasive surgical procedure using local or general anesthesia. The conjunctiva is separated from the sclera, the retinal tear is localized, and subretinal fluid is drained by cutting through the sclera and choroid. The retinal tear is coagulated using, for example, an argon laser. An implant, such as a sponge or piece of silicone, is then sutured over the sclera, pushing the eye wall inward and supporting the retinal tear from the outside. The patient requires about ten days to recover. Disadvantages are that the patient must undergo a surgical procedure and endure a long recovery period, and must tolerate the presence of a buckle around the eye that might interfere with movement of the eye.

Retinal reattachment by pneumatic retinopexy does not involve opening the conjunctiva, but instead involves injecting an expanding biocompatible gas into the vitreous cavity. About 0.3-0.5 ml of such a gas is injected into the vitreous cavity, where the gas expands from about three to about six times its volume. The patient is instructed to maintain a strict head position, allowing the expanded gas bubble to tamponade the retinal tear. However, the force of injection itself can force the subretinal fluid through the tear into the vitreous cavity. Cryocoagulation may be applied to the retinal tear to create scar tissue, closing the retinal tear. Alternatively, the subretinal fluid may resorb by itself within about 24 hours, after which laser coagulation can be performed.

There are several disadvantages of pneumatic retinopexy. Only superior tears can be treated, because air and gas rise above the vitreous fluid, and multiple tears that are separate from each other are difficult to tamponade. Subretinal fluid that is forced into the vitreous cavity may allow proliferation of retinal pigment epithelium cells, which can form membranes and create proliferative vitreoretinopathy (PVR). PVR may further detach the retina and is a serious complication of pneumatic retinopexy. Injection of gas without drainage of fluid may cause a rapid rise in intraocular pressure, thus the patient must be monitored postoperatively for several hours. If needed, the anterior chamber of the eye may be taped and systemic medication may be administered to lower the intraocular pressure. Possible side effects, however, are closure of the central retinal artery which could result in diminished blood flow to the retina. Additionally, in older individuals, the strict head positioning required to effect treatment may be very difficult to achieve and maintain. Still further, the results are unpredictable and a 24 hour waiting period is required to determine if the subretinal fluid has resorbed.

Retinal reattachment using vitrectomy with a tamponading agent is a surgical procedure, requiring local or general anesthesia. Three instruments are placed inside the eye: one is used for infusing fluid, one is used for cutting and removing tissue, and one is used for illumination. The vitreous gel is cut using a vitrectomy instrument and is removed, the intraocular fluid is simultaneously removed with the subretinal fluid, and the intraocular fluid is simultaneously replaced with air or another gas. The retinal tear is coagulated using a laser, with the gas remaining inside the eye for a continuous tamponading effect. Scleral buckling may also be performed to achieve enhanced outcome; this has the attendant drawbacks that have previously been described.

Disadvantages of vitrectomy are that the patient must undergo a surgical procedure with the possibility of injury to the lens or retina during surgery, and has a 70% chance of postoperative cataract formation due to the vitrectomy and the injection of gas into the eye.

Improvements in methods of treating retinal detachment are therefore desirable.

SUMMARY OF THE INVENTION

One embodiment of the invention is an apparatus for removing fluid from a subretinal space as occurs with a detached retina. The apparatus comprises a guide tube that guides insertion and placement of a fluid withdrawal device within the subretinal space. The distal end of the guide tube is placed on an external surface of the eye, over the site of detachment. The surgeon advances the device, guided by the tube, through the conjunctiva, sclera, and choroid and into the subretinal space. Fluid is then withdrawn from the space in a number of possible ways, for example, by negative pressure using manual or regulated vacuum, wicking action, gravity, etc.

The apparatus may contain additional features to facilitate its placement in and/or on the eye. For example, the guide tube may contain structures or may be operatively connected to a vacuum source to stabilize its placement on the eye. The guide tube and/or fluid withdrawal device may contain fiber optics and/or controls (e.g., knobs, handles, etc.) for easy visualization of the site and manipulation of the apparatus.

Another embodiment of the invention is an apparatus having a guide tube, an advancing tube, and a fluid withdrawal device in telescopic relationship with each other. The guide tube is placed on the eye at the site of detachment, the advancing tube penetrates the eye, and the device is further advanced within the subretinal space. A device that is a wick or a flexible tube may remain in the eye for several hours, up to a day, to ensure complete fluid removal.

Another embodiment of the invention is an apparatus where the fluid withdrawal device is located externally to the guide. In this embodiment, the guide structure need not be a tube having an internal bore, but instead may be an elongated structure. The device is guided into the eye by structures such as channels, grooves, etc. that are located on or are contained within the outer surface of the guide.

In another embodiment, the fluid withdrawal device is a solid pin that is connected to a diathermy unit. As the device is advanced, the overlying ocular structure is heated to facilitate penetration into the subretinal space. Fluid from the subretinal space may be drained under the conjunctiva.

Another embodiment of the invention is a method for removing fluid from a subretinal space in the eye of a patient having a detached retina. With the patient under a local anesthetic, the surgeon visualizes the site of detachment and positions the apparatus on the eyeball over the site. The surgeon then advances the fluid withdrawal device, guided by the tube, so that it is placed within the subretinal space and withdraws the fluid. This is a minimally invasive procedure that allows the patient to be ambulatory immediately afterwards and no strict head positioning is required. Thus, the method is an improvement for patients suffering from retinal detachments, such as patients with diabetic retinopathy. Further, the surgeon may introduce a fluid into the vitreous space after withdrawing the subretinal fluid to maintain intraocular pressure.

The invention will be further appreciated with respect to the following drawings and detailed description.

DETAILED DESCRIPTION

Figure 2:
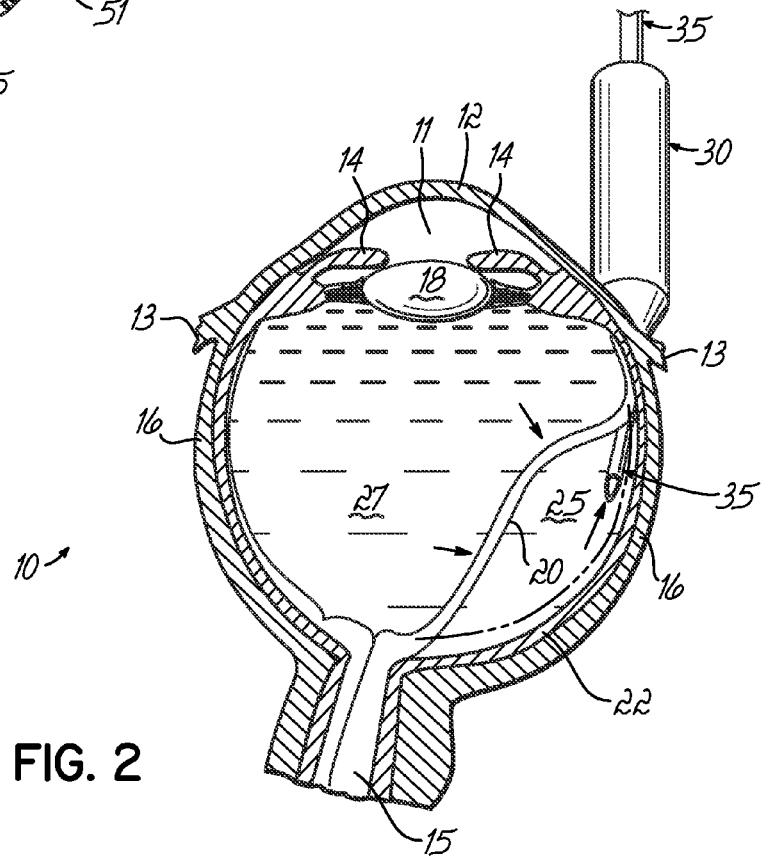
FIG. 2 shows a cross-section of an eye during treatment of retinal detachment using the inventive apparatus.

One embodiment of the invention is an apparatus for repairing a detached retina in an eye 10, shown in FIG. 2. The locations of the anterior chamber 11, cornea 12, conjunctiva 13, iris 14, optic nerve 15, sclera 16, lens 18, retina 20 and choroid 22 are illustrated.

With reference to FIGS. 1, 1A, 4, 4A, and 5, the apparatus 30 may be a fluid withdrawal device 35, such as a needle or hollow tubing, through which fluid may flow, and a guide tube 37 or probe for directing accurate advancement, placement, alignment, and/or positioning of the device 35. In one embodiment, the device 35 is a hollow needle for insertion into a subretinal space 25 of an eye 10, and withdrawal of fluid from the subretinal space 25 through the device 35. The needle gauge may range from 21 gauge to 41 gauge. In another embodiment, shown in FIG. 1A, the device 35 is a solid pin and fluid is removed from the subretinal space 25 by flowing adjacent the device 35, for example, by draining under the conjunctiva. In this embodiment, negative pressure facilitates fluid removal. In still another embodiment, shown in FIG. 5, the device 35 is a guide tube 37, an advancing tube 39, and fluid withdrawal device 42 within the bore 40 of the advancing tube 39 in a telescopic relationship. The guide tube 37 and advancing tube 39 may be withdrawn from the eye 10 while the device 42 remains in the subretinal space 25 for further withdrawal of fluid. In this embodiment, the device 42 is a flexible tube or a wick that may be made of any biocompatible material, such as polyethylene, silicon, nylon, TEFLON™ etc., or a wick that may be made of any porous biocompatible material, such as methylcellulose.

Figure 1:
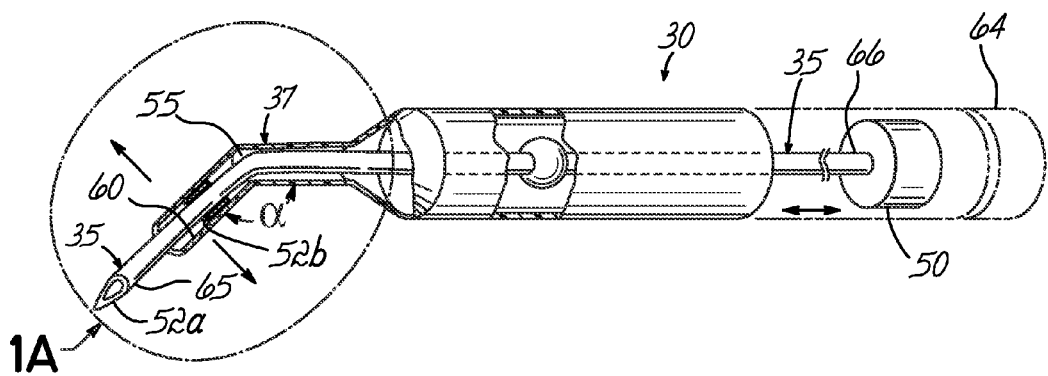
FIG. 1 shows one embodiment of the inventive apparatus for repairing a detached retina.

As shown in FIG. 1, the fluid withdrawal device 35 has a proximal end 66 and a distal end 65. The distal end 65 is advanced by the surgeon through the conjunctiva 13, sclera 16, and choroid 22 and placed or located within the subretinal space 25 of the eye 10. The proximal end 66 of the device 35 is used to control placement and/or positioning of the distal end 65 of the device 35. Fluid medication may also be inserted into the subretinal space 25 through the device 35, although its volume should be minimized to reduce the possibility of further retinal detachment.

Figure 3A:
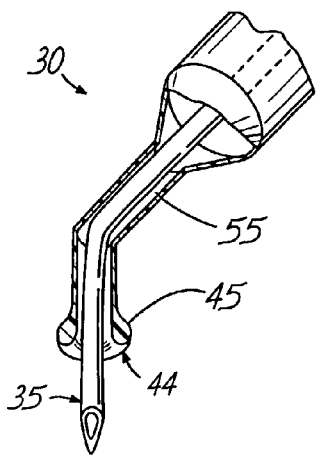
FIGS. 3A-C show embodiments of structures that facilitate use of the apparatus.
Figure 3B:
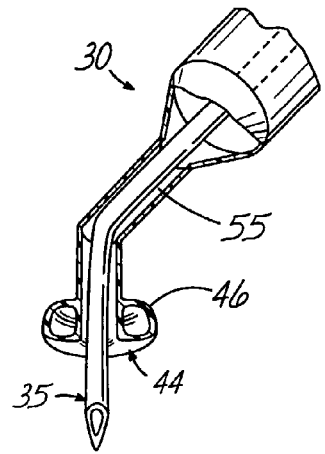
Figure 3C:
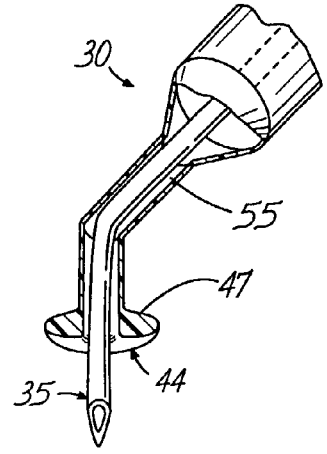
Figure 4:
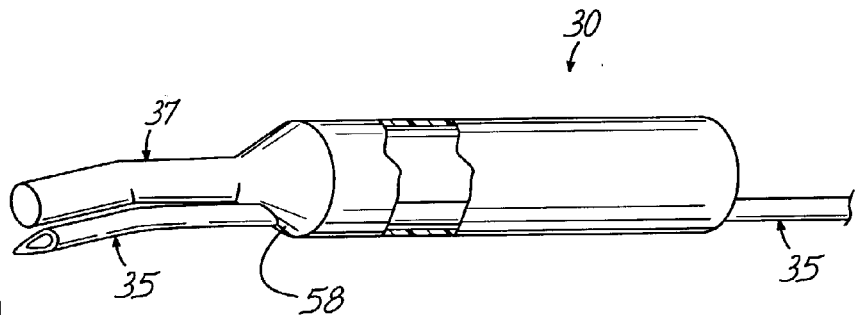
FIG. 4 shows an alternative embodiment of the apparatus of FIG. 1.
Figure 4A:
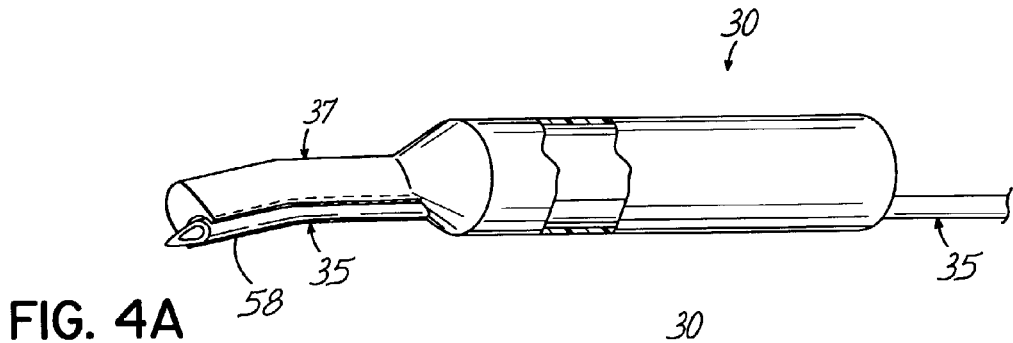
FIG. 4A is an additional alternative embodiment of the apparatus of FIG. 1.

The distal end 65 of the device 35 and/or guide tube 37 may assume a variety of shapes and configurations to allow for ease of advancement, insertion, placement, visualization, positioning, and stabilization of the apparatus 30. As shown in FIGS. 3A-C, for example, the distal end 65 of the device 35 and/or guide tube 37 may contain a fiber optic device 44 to improve the surgeon's visual field. The distal end 65 of the guide tube 37 may also be textured and/or contain one or more structures that assist to stabilize its placement on the exterior eye surface. As one example, the distal end 65 of the guide tube 37 may contain one or more grooves, ribs, or other structures to impart a less than smooth surface. As other examples, the distal end 65 may be widened to enhance its contact area, it may have a rounded end surface 45, a ballooned end surface 46, and/or a footed end surface 47, etc., and/or it may be operatively connected to a source of negative pressure to stabilize it on the exterior eye surface.

Figure 1A:
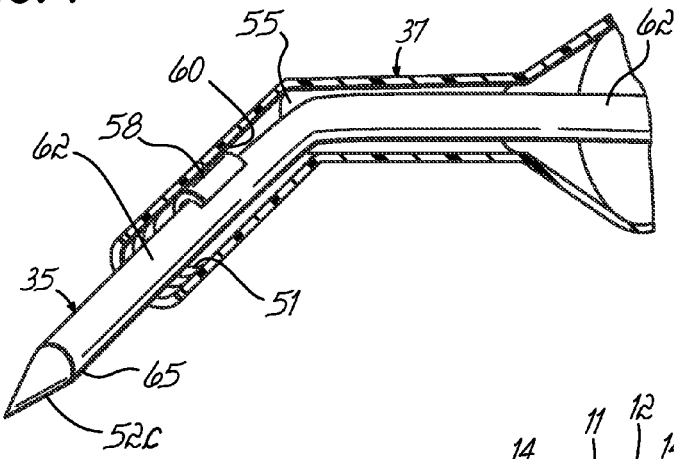
FIG. 1A is an exploded view of the encircled area of FIG. 1 showing an alternative embodiment and additional features of the apparatus.

Other embodiments of the apparatus 30 facilitate its penetration from the exterior eye surface at the site of detachment through the conjunctiva 13, sclera 16, and choroid 22 and into the subretinal space 25. As one example, the distal end 65 of the device 35 may be beveled 52a. As another example, the distal end 65 of the device 35 may be operatively connected to a vibrator, motor, etc. to controllably vibrate or actuate the device 35 for controlled advancement and penetration into the subretinal space 25. Examples of such devices are known to those skilled in the art and may be similar to the type used in toothbrushes, massagers, power syringes, etc. The distal end 65 of the device 35 and/or guide tube 37 may further contain calibration indicators 51, as shown in FIG. 1A, to allow length of advancement and/or depth of penetration to be more accurately determined. For example, the thickness of the sclera 16 is typically about 1-2 mm, thus, the distal end 65 of the guide tube 37 may contain calibration indicators 51 at 1 mm intervals, giving the surgeon further assurance as to depth of penetration.

The proximal end 66 of the device 35, 42 may contain a control structure 50 to allow the surgeon more sensitive, and therefore more accurate, manipulations and control of the distal end 65 of the device 35, 42. The control structure 50 may take a variety of forms, such as a knob, as shown in FIG. 1, or a bulb, a curved piece, a handle, a grip, a projection, a button, etc. (not shown). Any structure or device that will permit more sensitive manual control of the distal end 65 of the device 35, 42 and/or regulation of fluid flow through or adjacent the device 35, 42 is contemplated. The control structure 50 may additionally allow the surgeon to advance and retract the device 35, 42.

In one embodiment, the proximal end 66 of the fluid withdrawal device 35 may also be operatively connected to a syringe 64 (shown in phantom in FIG. 1) to exert a vacuum, either manually or using a controlled vacuum source (not shown). This allows controlled removal of fluid from the subretinal space 25 by negative pressure. A vacuum pressure in the range of about 1 mm Hg to about 100 mm Hg may be used. In another embodiment, one or more wicks 52b may be the fluid withdrawal device 35, 42. Fluid is withdrawn from the subretinal space 25 by wicking the fluid up through the wick 52b, in effect acting as a sponge. The wick 52b may be made of any porous biocompatible natural or synthetic material, such as methylcellulose or other polymer. The wick 52b, inserted using the guide tube 37 in telescopic relationship with advancing tube 39, may remain in the subretinal space 25 after the treatment, and could be removed any time up to about twenty-four hours thereafter.

The guide tube 37 may be made of any material that is sufficiently non-deformable so that the apparatus 30 is stable when it is located on the exterior surface of the eye 10. For example, it may be of the same material as a disposable syringe, it may be metal, etc. At least a portion of the fluid withdrawal device 35 may be flexible, with the distal end 65 sufficiently rigid to penetrate into the eye 10. The distal end 65 of the device 35 may form an angle α for ease of placement in the subretinal space 25. The angle α may be about 45°, about 90°, or any other degree that the surgeon finds convenient for proper placement of the device 35. The angle α of the distal end 65 of the device 35 may also be adjustable to accommodate a particular surgeon's preference and/or patient size.

The guide tube 37 guides or controls advancement, placement, manipulation, alignment, etc. of the device 35. In one embodiment, shown in FIG. 1A, the internal wall 60 of the guide tube 37 and the external wall 62 of the device 35 define a cavity 55. Fluid from the subretinal space 25 may flow in the cavity 55 through the length of the guide tube 37, either in place of or in addition to fluid flow through the device 35, depending upon whether the device 35 is hollow and thus permits fluid flow, or whether it is solid and does not permit fluid flow. In another embodiment, the cavity 55 defined by the internal wall 60 of the guide tube 37 and the external wall 62 of the device 35 is occluded, filled, etc., either selectively or non-selectively, so that fluid flow is channeled (e.g., through or adjacent the device 35).

The device 35 may be advanced and retracted within the guide tube 37, denoted by the doubleheaded arrow in FIG. 1. The surgeon may use a control structure at the proximal end 66 of the device 35 to selectively advance and retract its distal end 65. For example, it may be beneficial to retract a beveled distal end 52a of the device 35 to protect ocular structures until the device 35 is within or close to the subretinal space 25. The distal end 65 of the device 35 is then advanced, allowing the bevel 52a to facilitate fluid flow.

In another embodiment, the guide tube 37 contains a seating structure 58 for the device 35. The structure 58 may be located uniformly throughout the length of the tube 37, or it may be located intermittently at regular or irregular intervals, or it may be at only one location, to accommodate at least a portion of the device 35 sufficient to guide the device 35. The structure 58 may take a variety of forms, such as one or more of a groove, indentation, channel, conduit, holder, etc. and it may be either configured within or added to the external wall of guide tube 37. The guide tube 37 may enclose or abut the device 35. In the embodiment shown in FIGS. 4 and 4A, the seating structure 58 is on or within the outer surface of the guide tube 37.

The invention is also directed to a method for treating a patient for a detached retina 20 by removing fluid from a subretinal space at the site of detachment, thereby allowing the detached retina to flatten. The surgeon non-invasively visualizes the site of detachment, for example, through the pupil, by indirect ophthalmoscopy, or by ultrasound. The apparatus 30, as previously described, is then placed and stabilized on the exterior surface of the eye 10 substantially at the site of the detachment. The surgeon then controllably advances the device 35, guided by the guide tube 37, so that the distal end of the device 35 is within the subretinal space 25. Fluid is withdrawn and the detached retina 20 flattens.

The patient may be provided with an anesthetic applied locally to the eye 10. Examples of such local anesthetics include lidocaine or Optaine (Alcon Laboratory). The patient is ambulatory after the procedure and is not restricted as to either head and/or body movement. Moreover, because the conjunctiva is not cut, the procedure is only minimally invasive, and minimal or no recovery time is needed, as would be necessary for a more invasive surgical procedure. The patient is free to resume normal activities as soon as he/she feels capable of doing so.

Once the device 35 is positioned in the subretinal space 25, its location may be verified. Verification methods include x-ray, ultrasound, indirect ophthalmoscopy, optical coherence tomography, etc.

Fluid withdrawal from the subretinal space 25 may be accomplished by manual and/or mechanical methods. Manual methods include finger compression at the opening of the proximal end 66 of the device 35 to effect gravity flow, use of a syringe attachment to effect negative pressure, etc. Automated methods include application of a controlled vacuum from a vacuum source (not shown).

After withdrawal of fluid from the subretinal space 25, the surgeon may introduce a fluid into the vitreous cavity 27, thereby normalizing intraocular pressure. Liquids, such as saline, perfluorocarbon, or a low viscosity silicone oil, and/or gases such as air or perfluorocarbon, may be introduced. An mixture of air and another gas may also be used for an additional tamponading effect on the retina 20. In addition, the surgeon may use the apparatus 30 to introduce a fluid medicament containing one or more desired agents back into the subretinal space 25, the volume minimized so that further detachment of the now-flattened retina 20 does not occur. These agents may also be introduced into the vitreous cavity 27 as previously described, and/or under the retina 20 and include growth factors, anti-proliferative agents, antibiotics, immunological agents such as steroids, etc. They may be in the form of a liquid or an emulsion. Such agents may facilitate wound healing, limit inflammation, prevent infection, etc.

Figure 5:
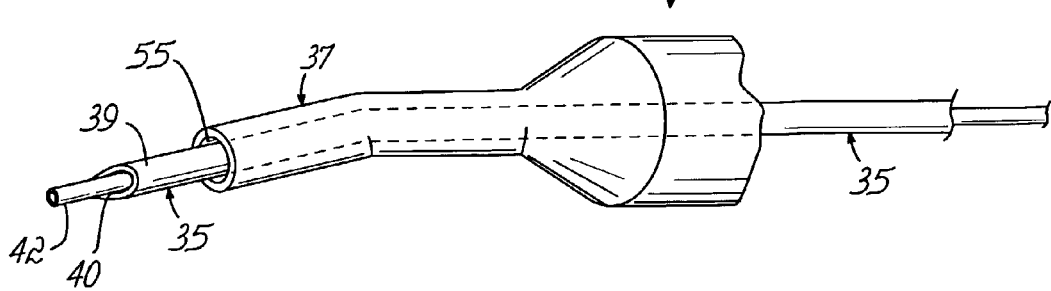
FIG. 5 shows another alternative embodiment of the apparatus of FIG. 1.

In one embodiment of the method, shown in FIG. 5, a telescopic arrangement of a guide tube 37, advancing tube 35, and fluid withdrawal device 42 of a wick or flexible hollow tube may be used. The fluid withdrawal device 42, once positioned in the subretinal space 25, may remain in the eye 10 for a desired period of time to ensure complete or continuous fluid removal. In this embodiment, the advancing tube 35 and guide tube 37 are removed, and the device 42 remains in the subretinal space 25 for up to about a day after the procedure. Variables affecting this duration include adequate fluid drainage, retinal flattening, patient tolerance, etc.

Figure 6:
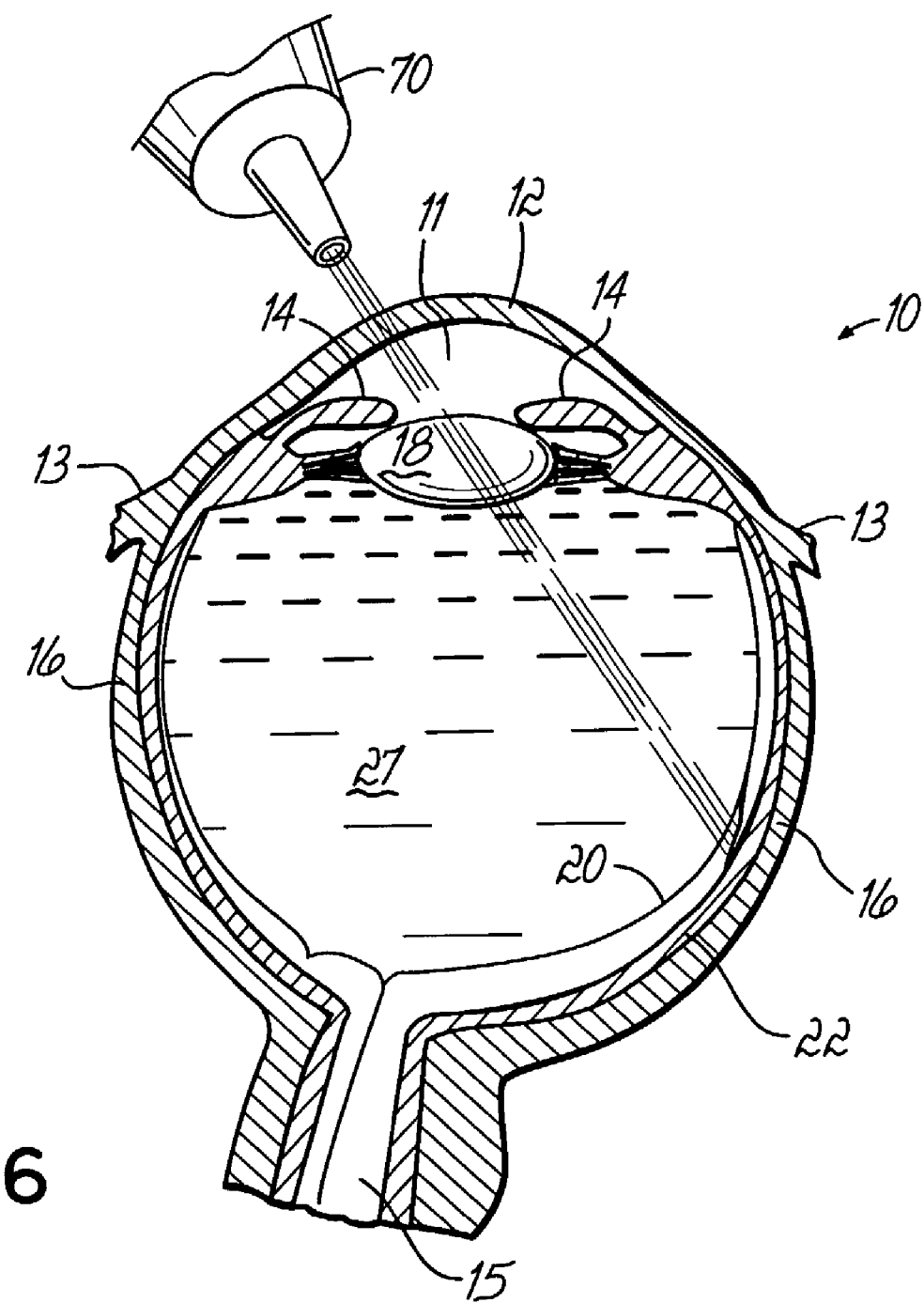
FIG. 6 shows the cross-section of the eye of FIG. 2 after treatment with laser applied to close the space at the site of retinal detachment.

Once fluid is withdrawn from the subretinal space 25 and the retina 20 is substantially flattened against the underlying structure, the retina 20 is reattached. Reattachment may occur by any method or combination of methods known to one skilled in the art, such as cryocoagulation or therapy with a laser 70, as shown in FIG. 6.

In another embodiment of the method, and with reference to FIG. 1A, a device 35 that is inserted into the subretinal space 25 is a solid pin 52c, made of a heat conducting material such as metal. It is guided by a guide tube 37, which may be as previously described, that is, it may be fully or partially grooved or otherwise marked for alignment or seating of the pin 52c. The pin 52c may be operatively connected to a diathermy unit for raising the temperature of the pin 52c. The pin 52c is controllably guided using the tube guide 37 into the subretinal space 25. Heating facilitates penetration into the subretinal space 25 through the the conjunctiva 13, sclera 16, and choroid 22 at the site of the detached retina 20. Fluid is removed from the subretinal space 25 at the site of puncture, that is, fluid is drained under the conjunctiva 13. In one embodiment, a diathermy unit (not shown), such as the type manufactured by Mira (Boston Mass.) is set to achieve a temperature in the eye in the range of about 48° C. to about 120° C. In another embodiment, the diathermy unit is set to achieve a temperature in the range of about 48° C. to about 90° C.

In addition to the above-described advantages of the method, the removal of subretinal fluid enhances complete reattachment of the retina. This is achieved without increased intraocular pressure, because the volume of fluid lost is immediately replaced. The method uses only a minimally invasive procedure, providing less risk of surgical complications, injury to the lens, and scarring of the conjunctiva. Additionally, because the fluid is not emptied or withdrawn into the vitreous cavity, the possibility of progressive vitreous retinopathy is decreased.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

What is claimed:

1. A method for removing fluid from a subretinal space in the eye of a patient having a detached retina, the method comprising
    visualizing the detachment site,
    positioning on an external surface of the eye at the detachment site an apparatus comprising a guide tube and a fluid withdrawal device, the guide tube having proximal and distal ends and defining an internal bore at least partially containing the device, a terminus of the tube at the distal end contacting the external surface of the eye and being stabilized on the exterior eye surface, the device capable of movement relative to the guide tube,
    advancing the device into the subretinal space guided by the guide tube,
    withdrawing fluid from the subretinal space, and
    introducing a fluid into a vitreous space after withdrawing the subretinal fluid.

2. The method of claim 1 wherein advancement of the device is guided by a control structure at the proximal end of the device and/or guide tube.

3. The method of claim 1 wherein the patient has diabetic retinopathy.

4. The method of claim 1 further comprising verifying the placement of the device within the subretinal space.

5. The method of claim 1 wherein the fluid introduced into the vitreous space is selected from the group consisting of saline, air, perfluorocarbons, low viscosity silicone oil, and combinations thereof.

6. The method of claim 1 wherein the apparatus stabilizes the eye during the method.

7. A method of repairing a retinal tear resulting in retinal detachment and through which fluid enters forming a fluid-filled subretinal space in an eye of a patient, the method comprising
    visualizing the detachment site,
    positioning an apparatus on an external surface of the eye over the detachment site, the apparatus comprising a guide tube having proximal and distal ends and defining an internal bore at least partially containing a fluid withdrawal device, a terminus of the tube at the distal end for positioning on an external surface of the eye at the detachment site and being stablized on the exterior eye surface, and the device at least partially contained therein, the device capable of movement relative to the guide tube,
    advancing the device into the subretinal space,
    removing the guide tube from the eye and maintaining the device in the subretinal space,
    withdrawing fluid from the space sufficient to flatten the retina, and
    coagulating the area surrounding the tear to close the tear.

8. The method of claim 7 wherein the device is selected from the group consisting of a needle, a wick, a flexible tube, a pin, and combinations thereof.

9. The method of claim 7 wherein the patient has diabetic retinopathy.

10. The method of claim 7 wherein the device remains in the subretinal space for up to about twenty-four hours.

11. The method of claim 7 further comprising retracting the device and thereafter removing the apparatus from the eye.

12. The method of claim 7 wherein the patient is ambulatory immediately following the procedure.

13. The method of claim 7 further comprising verifying placement of the device within the sub-retinal space.

14. The method of 13 wherein verification is by a method selected from the group consisting of ultrasound, x-ray, ophthalmoscope, optical coherence tomography, and combinations thereof.

15. The method of claim 7 wherein the device defines an internal bore further containing a wick or a flexible hollow tube that remains within the subretinal space after removing the guide tube and the device from the eye.

16. The method of claim 7 further comprising reattaching the detached retina by a method selected from the group consisting of laser coagulation, cryocoagulation, and combinations thereof.

17. A method of repairing a retinal tear resulting in retinal detachment and through which fluid enters forming a fluid-filled subretinal space in an eye of a patient, the method comprising visualizing the detachment site, positioning an apparatus on an external surface of the eye over the detachment site, the apparatus comprising a guide tube having proximal and distal ends and defining an internal bore at least partially containing a fluid withdrawal device, a terminus of the tube at the distal end for positioning on an external surface of the eye at the detachment site and being stabilized on the exterior eye surface, and the device at least partially contained therein, the device capable of movement relative to the guide tube, advancing the device into the subretinal space, withdrawing fluid from the space sufficient to flatten the retina, and coagulating the area surrounding the tear to close the tear, wherein the device defines an internal bore further containing a wick or a flexible hollow tube that remains within the subretinal space after removing the guide tube and the device from the eye.

* * * * *